US010722446B2

(12) United States Patent
Pimenta et al.

(10) Patent No.: US 10,722,446 B2
(45) Date of Patent: Jul. 28, 2020

(54) AQUEOUS ORAL CARE COMPOSITIONS

(75) Inventors: Paloma Pimenta, Staten Island, NY (US); Davide Miksa, Doylestown, PA (US); Shira Pilch, Highland Park, NJ (US); Aarti Rege, East Windsor, NJ (US); Richard Sullivan, Atlantic Highlands, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/362,908

(22) PCT Filed: Dec. 15, 2011

(86) PCT No.: PCT/US2011/065125
§ 371 (c)(1),
(2), (4) Date: Jun. 4, 2014

(87) PCT Pub. No.: WO2013/089734
PCT Pub. Date: Jun. 20, 2013

(65) Prior Publication Data
US 2014/0305461 A1 Oct. 16, 2014

(51) Int. Cl.
A61K 8/81 (2006.01)
A61K 8/44 (2006.01)
A61Q 11/00 (2006.01)
A61K 8/21 (2006.01)
A61K 8/73 (2006.01)

(52) U.S. Cl.
CPC ............. *A61K 8/8152* (2013.01); *A61K 8/21* (2013.01); *A61K 8/44* (2013.01); *A61K 8/73* (2013.01); *A61K 8/731* (2013.01); *A61Q 11/00* (2013.01); *A61K 2800/594* (2013.01)

(58) Field of Classification Search
None
See application file for complete search history.

(56) References Cited

U.S. PATENT DOCUMENTS

| 3,943,063 A | 3/1976 | Morishita et al. | |
| 5,137,729 A | 8/1992 | Kuroya et al. | |
| 5,202,112 A * | 4/1993 | Prencipe | A61Q 11/00 424/52 |
| 5,284,648 A | 2/1994 | White | |
| 5,562,939 A | 10/1996 | Lewis | |
| 5,776,435 A | 7/1998 | Gaffar et al. | |
| 6,106,883 A | 8/2000 | Sokolik et al. | |
| 6,153,210 A | 11/2000 | Roberts et al. | |
| 6,294,186 B1 * | 9/2001 | Beerse et al. | 424/405 |
| 6,595,997 B2 | 7/2003 | Axelson, Jr. et al. | |
| 6,596,298 B2 | 7/2003 | Leung et al. | |
| 6,602,841 B1 | 8/2003 | Becker et al. | |
| 6,682,721 B2 | 1/2004 | Kim et al. | |
| 6,683,067 B2 | 1/2004 | Lawter et al. | |
| 7,008,979 B2 | 3/2006 | Schottman et al. | |
| 2003/0158111 A1 * | 8/2003 | Bar-Or | 514/12 |
| 2004/0101494 A1 | 5/2004 | Scott et al. | |
| 2007/0122358 A1 * | 5/2007 | Wang | A61K 8/25 424/52 |
| 2007/0122359 A1 | 5/2007 | Wang et al. | |
| 2008/0267891 A1 * | 10/2008 | Zaidel | A61K 8/25 424/50 |
| 2009/0238777 A1 | 9/2009 | Joziak | |
| 2010/0135921 A1 * | 6/2010 | Hughes | A61K 8/25 424/49 |
| 2010/0135932 A1 * | 6/2010 | Deckner | A61K 8/25 424/52 |
| 2010/0316580 A1 * | 12/2010 | Kohli | A61K 8/21 424/52 |
| 2011/0014136 A1 | 1/2011 | Kohli et al. | |
| 2011/0256074 A1 | 10/2011 | Corcoran-Henry | |

FOREIGN PATENT DOCUMENTS

| CN | 102223921 | 10/2011 |
| DE | 202008006245 | 8/2008 |
| EP | 056966 A2 * | 11/1993 |
| RU | 2116781 | 8/1998 |
| TW | 200934517 | 8/2009 |
| WO | WO 00010527 | 3/2000 |
| WO | WO 00/49994 | 8/2000 |
| WO | WO 05041876 | 5/2005 |
| WO | WO 06013081 | 2/2006 |
| WO | WO 2009/100264 | 8/2009 |
| WO | WO 2009/100277 | 8/2009 |
| WO | WO 09117644 | 9/2009 |
| WO | WO 10066655 | 6/2010 |
| WO | WO 12087324 | 6/2012 |
| WO | WO 12087325 | 6/2012 |

(Continued)

OTHER PUBLICATIONS

Marcotte et al. Evaluation of Rheological Properties of Selected Salt Enriched Food Hydrocolloids, Journal of Food Engineering 48 (157-167). (Year: 2001).*
Cooper, "Colgate Dry Mouth Relief Fluoride Mouthwash," Dentaltradeonline (internet publication) http://www.dentaltradeonline.com.au/index.php?option=com_content&view-article&id=98%3Acolgate-dry-mouth-relief-fluoride-mouthwash&catid=35%3Aadvertori (Aug. 4, 2011) XP002686427.
Hooper; et al., "The protective effects of toothpaste against erosion by orange juice: Studies in situ and in vitro," Journal of Dentistry vol. 35, 2007, pp. 476-481.
International Search Report and the Written Opinion issued in International Application PCT/US2011/65125 dated Dec. 3, 2012. WO.

(Continued)

*Primary Examiner* — David J Blanchard
*Assistant Examiner* — Sarah J Chickos

(57) ABSTRACT

Described herein are aqueous oral care compositions comprising (a) an effective amount of a basic amino acid in free or orally acceptable salt form; and (b) a polymer system comprising (i) a cellulosic polymer, (ii) a gum polymer, and (iii) a polyacrylate polymer or co-polymer; and methods of making and using the same.

16 Claims, No Drawings

(56) References Cited

FOREIGN PATENT DOCUMENTS

| WO | WO 12087326 | 6/2012 |
|---|---|---|
| WO | WO 12087327 | 6/2012 |
| WO | WO 12087328 | 6/2012 |

OTHER PUBLICATIONS

Reijden Van Der W A et al, "Rheological Properties of Commercially Available Polysaccharides With Potential Use in Saliva Substitute," Biorheology. Elsevier Science Ltd., vol. 31. No. 6., Jan. 1, 1994, pp. 631-642. XP000577817, ISSN: 0006-355X, Oxford, GB.
Written Opinion of the International Preliminary Examining Authority issued in International Application PCT/US2011/65125 dated Dec. 4, 2013. WO.
Chinese Search Report issued in corresponding Chinese Patent Application No. 201180075496.3 dated Feb. 27, 2015.
"Colgate Dry Mouth Relief", Colgate Oral Pharmaceuticals, Inc., Retrieved Jul. 8, 2015 rom the Internet, http://www.drugs.com/otc/109054/colgate-dry-mouth-relief.html.
V.I. Chueshev, Promishlennaya tekhnologya lekarstv, vol. 1, Kharkov, izdatelstvo NFAU, 2002, p. 24.
Adair et al., 2001, "Recommendations for Using Fluoride to Prevent and Control Dental Caries in the United States." CDC Morbidity and Mortality Weekly Report, Aug. 17, 2001, 50(RR14):1-42.
Karsa et al., ed., 1996, "6. Recent Work on Poly(Acrylic Acid) Systems," in: Chemical Aspects of Drug Delivery Systems, The Royal Society of Chemistry, Special Publication No. 178, p. 22.
Laba, ed., 1993, "V. Synthetics," in Rheological Properties of Cosmetics and Toiletries Marcel Dekker, Inc., New York, Basel 13:99-103.
Von Jurgen Falbe, et al., ed., 1997, "Fluoridierung," Rompp Lexikon fir Chemie, Thieme Verlag, 10th ed., p. 1388.

* cited by examiner

AQUEOUS ORAL CARE COMPOSITIONS

CROSS-REFERENCE TO RELATED PATENT APPLICATIONS

The present application is a U.S. national stage entry under 35 U.S.C. § 371 of Patent Cooperation Treaty Patent Application No. PCT/US2011/65125, filed Dec. 15, 2011, the entirety of which is incorporated herein by reference.

BACKGROUND

Conventional mouthwash products may contain antibacterial agents and/or fluoride, but they generally do not prevent or repair the acid channels, or enhance the delivery and retention of active agents. Efficacious protection against such acid attacks to the tooth surface should ideally provide a physical barrier against the acid attack, as well as enhance delivery and retention of an active agent that can neutralize the acid and/or strengthen the tooth enamel.

SUMMARY

In some embodiments, the present invention provides an aqueous oral care composition comprising an effective amount of a basic amino acid, in free or orally acceptable salt form, and a polymer system comprising (i) a cellulosic polymer, (ii) a gum polymer, and (iii) a polyacrylate polymer or co-polymer, e.g., wherein the mouthwash displays (i) a measurable degree of viscoelasticity with a ratio of elastic to viscous components, G'/G", greater than 0.5 and (ii) shear thinning behavior with a flow rate index, n, of less than 0.85. In some embodiments, the composition is a viscoelastic mouthwash. In some embodiments, the mouthwash optionally further comprises an effective amount of a fluoride source.

The high viscoelasticity of the formulation (G'/G">0.5) favors the formation of a polymer film on the tooth surface and greater retention of actives such as fluoride, arginine or buffering agents onto the enamel surface. The shear thinning property (n<0.85) further characterizes the mouthwash as viscoelastic and non-Newtonian and helps drive the consumer acceptability of the mouthwash.

As demonstrated by the examples below, the compositions of the present invention provide improved resistance to enamel erosion. Without being bound by theory, it is believed that the use of mucoadhesive polymers at concentrations sufficient for the polymers to overlap significantly and form a network in solution results in the deposition of a polymer film on hard and soft tissues of the oral cavity upon usage. This polymer film serves as a physical barrier against erosive acids, as well as a carrier to enhance the delivery and retention of fluoride and/or basic amino acids such as arginine onto enamel surfaces, therefore providing superior enamel protection against acid induced erosion and demineralization. Moreover, it is believed that the uptake of the basic amino acid, e.g., arginine, is enhanced because basic amino acids such as arginine are positively charged. In the presence of a polymer network that is largely negative charged, the charge and charge interaction enhances the deposition of the basic amino acid to oral surfaces.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

Some embodiments of the present invention provide an aqueous oral care composition comprising an effective amount of a basic amino acid in free or orally acceptable salt form and; a polymer system comprising (i) a cellulosic polymer, (ii) a gum polymer, and (iii) a polyacrylate polymer or co-polymer; wherein the composition has a flow rate index of less than 0.85.

Some embodiments further comprise a fluoride source; wherein the fluoride source. In some embodiments, the fluoride source is present in an amount effective to provide from about 90 to about 500 ppm of fluoride. In other embodiments, the fluoride source is present in an amount effective to provide about 225 ppm of fluoride.

In some embodiments, the fluoride source is selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and a combination of two or more thereof.

In some embodiments, the fluoride source is selected from sodium fluoride; sodium monofluorophosphate; and a combination thereof. In other embodiments, the fluoride source comprises sodium fluoride.

In some embodiments, the basic amino acid comprises L-arginine in free or orally acceptable salt form. In some embodiments, the basic amino acid is selected from arginine free base, arginine hydrochloride, arginine phosphate, arginine bicarbonate, and combinations thereof. In some embodiments, the effective amount of the basic amino acid in free or orally acceptable salt form comprises 0.05 to 2% by weight of the formulation (measured as the weight of the free base equivalent when in orally acceptable salt form).

Some embodiments further comprise a buffering agent. In some embodiments, the buffering agent is a sodium phosphate buffer (e.g., sodium phosphate monobasic and disodium phospate).

Other embodiments further comprise a humectant, e.g., selected from glycerin, sorbitol, propylene glycol, and a combination of two or more thereof.

Still other embodiments further comprise an antibacterial agent, e.g., triclosan or cetylpyridinium chloride.

The composition of any of the foregoing claims wherein the cellulosic polymer is selected from a hydroxyalkyl methyl cellulose; a carboxyalkyl methylcellulose; a hydroxyalkyl cellulose; an alkyl cellulose; a carboxyalkyl cellulose, and a combination of two or more thereof.

Some embodiments provide an aqueous oral care composition comprising: from about 0.5% to about 2%, by weight, of a basic amino acid in free or orally acceptable salt form; a polymer system comprising (i) a cellulosic polymer, (ii) a gum polymer, and (iii) a polyacrylate polymer or co-polymer; and from about 0.01 to about 0.5%, by weight, of a fluoride source; wherein the composition has a flow rate index of less than 0.85; and wherein the composition delivers an amount of fluoride effective to provide a step height difference of less than 0.25 microns, when evaluated using the Hooper protocol.

In some embodiments, the fluoride source is present in an amount from about 0.02% to about 0.2%, by weight, of the composition. In some embodiments, the fluoride source is present in an amount from about 0.03% to about 0.08%, by weight, of the composition. Other embodiments provide a composition wherein the fluoride source is present in the amount of about 0.05%, by weight, of the composition. In some embodiments, the fluoride source is present in the amount of 0.5%, by weight, of the composition.

Some embodiments of the present invention provide a method of reducing dental enamel erosion comprising administering any one of the compositions described herein to the oral cavity of subject in need thereof. In some embodiments, the administering comprises rinsing for from about 15 to about 60 seconds. In some embodiments, the administering comprises rinsing for from about 30 seconds.

Some embodiments of the present invention thus provide, a viscoelastic mouthwash (Mouthwash 1) comprising (a) an effective amount of a basic amino acid in free or orally acceptable salt form and (b) a polymer system comprising (i) a cellulosic polymer, (ii) a gum polymer, and (iii) a polyacrylate polymer or co-polymer.

In some embodiments, the cellulosic polymer is selected from hydroxyalkyl methyl celluloses (such as hydroxypropyl methyl cellulose, hydroxybutyl methyl cellulose, hydroxyethyl methyl cellulose, hydroxymethyl methyl cellulose and hydroxyethylpropyl methyl cellulose); carboxyalkyl methylcelluloses (such as carboxypropyl methyl cellulose, carboxybutyl methyl cellulose, carboxyethyl methyl cellulose, carboxymethyl methyl cellulose and carboxyethylpropyl methyl cellulose); hydroxyalkyl celluloses (such as hydroxypropyl cellulose, hydroxybutyl cellulose, hydroxyethyl cellulose, hydroxymethyl cellulose and hydroxyethylpropyl cellulose); alkyl celluloses (such as propyl cellulose, butyl cellulose, ethyl cellulose, methyl cellulose); carboxyalkyl celluloses (such as carboxypropyl cellulose, carboxybutyl cellulose, carboxyethyl cellulose, carboxymethyl cellulose and carboxyethylpropyl cellulose), and combinations thereof.

In some embodiments, the cellulosic polymer comprises carboxymethyl cellulose.

In some embodiments, the gum polymer is selected from carrageenan gum, xanthan gum, and combinations thereof. In some embodiments, the gum polymer comprises xanthan gum. In some embodiments, the polyacrylate polymer or co-polymer is a carbomer. In some embodiments, the polyacrylate polymer or co-polymer is selected from homo- and copolymers of acrylic acid crosslinked with a polyalkenyl polyether.

In some embodiments, the compositions comprise the ingredients in the concentration ranges provided in Table 1 (below).

TABLE 1

| Ingredient | Conc. Range % wt/wt |
| --- | --- |
| Water | 50.0-90.0 |
| Humectants | 1.0-25.0 |
| Surfactant | 0.01-10.0 |
| Sodium phosphate monobasic | 0.01-5.0 |
| Disodium phosphate | 0.01-5.0 |
| Preservative | 0.01-1.0 |
| Flavor | 0.01-1.0 |
| Cellulosic polymer | 0.01-0.5 |
| Gum polymer | 0.01-0.5 |
| Polyacrylate polymer or co-polymer | 0.01-0.5 |
| Sodium fluoride | 0-0.05 |

TABLE 1-continued

| Ingredient | Conc. Range % wt/wt |
| --- | --- |
| Arginine (in free or salt form, by weight of the free base) | 0.05-2.0 |
| Sweetener | 0.001-0.5 |
| Cetylpyridinium chloride | 0.001-1.0 |

Viscoelastic mouthwash formulations are described in the following co-pending applications PCT/US 2010/061962, PCT/US 2010/061956, and PCT/US 2010/061959, all filed Dec. 23, 2010, the contents of which are incorporated herein by reference in their entirety.

The compositions of the present invention are carefully tailored with the right combination and concentration of polymers to form a viscoelastic, low viscosity aqueous solution that possess unique rheology but still resembles the fluidity of a typical mouthwash.

As used herein, the term "viscoelastic fluid" refers to a complex fluid that exhibits mechanical properties that are both elastic (solid-like e.g. rubber) and viscous (liquid-like, flowable e.g. water). A viscoelastic fluid composition will deform and flow under the influence of an applied shear stress (e.g. shaking or swishing in the mouth), but when the stress is removed the composition will recover from the deformation. The elastic portion of the viscoelastic behavior is quantified by the elastic modulus (G'), while the viscous portion is quantified by the viscous modulus (G").

As used herein, the term "shear thinning" refers to a property in which viscosity decreases with increasing rate of shear stress. Materials that exhibit shear thinning properties are called pseudoplastic.

As used herein, "structured fluid" and "structured composition" may be used interchangeably, and refer to a fluid that exhibits a G' value greater than the G" value (i.e. the ratio of G' to G" is >0.5) within the linear viscoelastic region of a strain sweep measurement. The ratio of G' to G" has been identified as the Structural Parameter.

The basic amino acids which can be used in the compositions of the present invention include not only naturally occurring basic amino acids, such as arginine, lysine, and histidine, but also any basic amino acids having a carboxyl group and an amino group in the molecule. Accordingly, basic amino acids include, but are not limited to, arginine, lysine, citrullene, ornithine, creatine, histidine, diaminobutanoic acid, diaminoproprionic acid, salts thereof or combinations thereof. In a particular embodiment, the basic amino acids are selected from arginine, citrullene, and ornithine, preferably, arginine, for example, L-arginine.

The compositions of the invention are intended for topical use in the mouth and so salts for use in the present invention should be orally acceptable, that is, safe for topical use in the mouth, in the amounts and concentrations provided. Suitable salts include salts known in the art to be pharmaceutically acceptable salts, which are generally considered to be orally acceptable for this purpose in the amounts and concentrations provided. Orally acceptable salts include those derived from pharmaceutically acceptable inorganic or organic acids or bases, for example acid addition salts formed by acids which form a physiological acceptable anion, e.g., hydrochloride salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

In some embodiments the compositions further comprise one or more components selected from a fluoride ion source; a tartar control agent; a buffering agent; an abrasive; and a combination of two or more thereof. In some embodiments, at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof.

Synthetic high molecular weight polymers of acrylic acid known as carbomer may be homopolymers of acrylic acid, crosslinked with an allyl ether pentaerythritol, allyl ether of sucrose or allyl ether of propylene. Carbomer has a USP classification of "carbomer homopolymer Type A". Carbomers have the ability to adsorb, retain water and swell to many times their original volume. Carbomers codes (910, 934, 940, 941, 971, 974 and 934P) are an indication of molecular weight and the specific components of the polymer. Carbomers are commercially available, under the trade name Carbopol® from Lubrizol and other companies.

Humectants useful herein include polyhydric alcohols such as glycerin, sorbitol, xylitol or low molecular weight PEGs, alkylene glycol such as polyethylene glycol or propylene glycol. In various embodiments, humectants are operable to prevent hardening of paste or gel compositions upon exposure to air. In various embodiments humectants also function as sweeteners. In some embodiments, the humectant is present in the amount of about 1 to about 40% each by weight. In some embodiments, the humectant is sorbitol. In some embodiments sorbitol present at a concentration of from about 5 to about 25%, by weight. In some embodiments sorbitol present at a concentration of from about 5 to about 15%, by weight. In some embodiments, the sorbitol is present at a concentration of about 10%, by weight. Reference to sorbitol herein refers to the material typically as available commercially in 70% aqueous solutions. In some embodiments, the total humectant concentration is from about 1 to about 60%, by weight. In some embodiments, the humectant is glycerin. In some embodiments, glycerin is present at a concentration of from about 5 to about 15%, by weight. In some embodiments, glycerin present is at a concentration of about 7.5%, by weight. In some embodiments, the humectant is propylene glycol. In some embodiments, propylene glycol is present at a concentration of about 5 to about 15%, by weight. In some embodiments, propylene glycol is present at a concentration of about 7%, by weight.

Some embodiments provide a composition wherein a preservative is present. In some embodiments, the preservative is selected from parabens, potassium sorbate, benzyl alcohol, phenoxyethanol, polyaminopropryl biguanide, caprylic acid, sodium benzoate and cetylpyridinium chloride. In some embodiments, the preservative is present at a concentration of from about 0.0001 to about 1%, by weight. In some embodiments, the preservative is present at a concentration of from about 0.01 to about 1%, by weight. In some embodiments, the preservative is present at a concentration of about 0.5%, by weight.

Colorants such as dyes may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-n-aphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sul-fophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-.DELTA.-3,5-cycl-ohexadienimine], FD&C Blue No. 1 (disodium salt of dibenzyldiethyldiamino-triphenylcarbinol trisulfonic acid anhydrite), FD&C Blue No. 2 (sodium salt of disulfonic acid of indigotin) and mixtures thereof in various proportions. Typically, colorants if included are present in very small quantities.

Flavor agents are known, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavor agents can be used individually or in admixture. Commonly used flavors include mints such as peppermint, artificial vanilla, cinnamon derivatives, and various fruit flavors, whether employed individually or in admixture. Generally, any flavoring or food additive, such as those described in Chemicals Used in Food Processing, publication 1274 by the National Academy of Sciences, pages 63-258, may be used. Typically, flavorants if included are present at 0.01-1%, by weight. In some embodiments, flavoring may be present in about 0.2%, by weight.

Sweeteners include both natural and artificial sweeteners. Suitable sweetener include water soluble sweetening agents such as monosaccharides, disaccharides and poysaccharides such as xylose, ribose, glucose (dextrose), mannose, galactose, fructose (levulose), sucrose (sugar), maltose, water soluble artificial sweeteners such as the soluble saccharin salts, i.e., sodium or calcium saccharin salts, cyclamate salts dipeptide based sweeteners, such a L-aspartic acid derived sweeteners, such as L-aspartyl-L-phenylalaine methyl ester (aspartame). In general, the effective amount of sweetener is utilized to provide the level of sweetness desired for a particular composition, will vary with the sweetener selected. This amount will normally be about 0.001% to about 5% by weight of the composition. In some embodiments, the sweetener is sodium saccharin and present at about 0.01% by weight of the composition.

Optional breath freshening agents may be provided. Any orally acceptable breath freshening agent can be used, including without limitation zinc salts such as zinc gluconate, zinc citrate and zinc chlorite, alpha-ionone and mixtures thereof. One or more breath freshening agents are optionally present in a breath freshening effective total amount.

Optionally, the composition may include a tartar control (anticalculus) agent. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents include polycarboxylate polymers and polyvinyl methyl ether/maleic anhydride (PVME/MA) copolymers, such as those available under the Gantrez™ brand from ISP, Wayne, N.J.

In some embodiments, tartar control agent is present at a concentration of from about 0.01 to 10%, by weight. In some embodiments, the tartar control agent is present at a concentration of about 1%, by weight. In some embodiments, the tartar control agent also acts as a buffer. For example, in a phosphate buffer system, sodium phosphate monobasic is present at a concentration of from about 0.01 to about 5%, by weight and disodium phosphate is present at a concentration of from about 0.01 to about 5%, by weight, the precise ratio depending upon the other excipients in the formulation and the desired pH.

Other optional additives include antimicrobial (e.g., antibacterial) agents. Any orally acceptable antimicrobial agent can be used, including triclosan (5-chloro-2-(2,4-dichlorophenoxy)phenol); zinc and stannous ion sources; quaternary ammonium compounds such as cetylpyridinium chloride (CPC); bisguanides such as chlorhexidine; and benzalkonium chloride. A further illustrative list of useful antibacterial agents is provided in U.S. Pat. No. 5,776,435 to Gaffar, et al. In some embodiments, antimicrobial agent is present at a concentration of from about 0.001 to about 1%, by weight. In some embodiments, the antimicrobial agent is cetylpyridinium chloride. In some embodiments, the cetylpyridinium chloride is present at a concentration of about 0.05%, by weight.

Antioxidants are another class of optional additives. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Also optional, saliva stimulating agent, useful for example in amelioration of dry mouth may be included. Any orally acceptable saliva stimulating agent can be used, including without limitation food acids such as citric, lactic, malic, succinic, ascorbic, adipic, fumaric, and tartaric acids, and mixtures thereof. One or more saliva stimulating agents are optionally present in a saliva stimulating effective total amount.

Optionally, an antiplaque (e.g., plaque disrupting) agent may be included. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

Optional desensitizing agents include potassium citrate, potassium chloride, potassium tartrate, potassium bicarbonate, potassium oxalate, potassium nitrate, strontium salts, and mixtures thereof. In some embodiments, a local or systemic analgesic such as aspirin, codeine, acetaminophen, sodium salicylate or triethanolamine salicylate can be used.

In some embodiments, the methods comprise the step of rinsing the oral cavity with a composition as described herein. In some embodiments, the shear thinning properties of the composition increase the flow and thus the area covered when agitated within the oral cavity. In some embodiments, a polymer film forms on the surface of the oral cavity following discharge of the composition which results in relief of dry mouth symptoms. In some embodiments, 5 ml or more of the composition is gargled. In some embodiments, 10 ml or more is used. In some embodiments, 10-50 ml is used. In some embodiments, 15-25 ml or more is used. In some embodiments, 15 ml or more is used. In some embodiments, the individual gargles with the composition multiple times per day. In some embodiments, the individual gargles with the composition on multiple days. In some embodiments, the individual gargles with the composition every 4 to 6 hours up to 6 times per day.

As used throughout, ranges are used as shorthand for describing each and every value that is within the range. Any value within the range can be selected as the terminus of the range. In addition, all references cited herein are hereby incorporated by referenced in their entireties.

In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1

The objective is to provide a viscoelastic mouthwash containing a polymer system plus an active (arginine, preferably with fluoride) for superior protection of enamel against acid induced demineralization. Mouthwash formulations are prepared with the following ingredients:

TABLE 2

| Mouthwash 1: Ingredients | Concentration (% wt/wt) |
| --- | --- |
| Water | 71.05 |
| Humectants | 17.5 |
| Surfactant | 1 |
| Sodium phosphate monobasic | 1 |
| Disodium phosphate | 0.15 |
| Preservative | 0.5 |
| Flavor | 0.2 |
| Carboxymethyl Cellulose | 0.083 |
| Xanthan Gum | 0.083 |
| Acrylate co-polymer | 0.05 |
| Sodium fluoride | 0.02 |
| Arginine (Arg $HCO_3$) | 1.3 |
| Sweetener | 0.01 |
| Cetylpyridinium chloride | 0.05 |

TABLE 3

| Mouthwash 2: Ingredients | Concentration (% wt/wt) |
| --- | --- |
| Water | 72.35 |
| Humectants | 17.5 |
| Surfactant | 1 |
| Sodium phosphate monobasic | 1 |
| Disodium phosphate | 0.15 |
| Preservative | 0.5 |
| Flavor | 0.2 |
| Carboxymethyl Cellulose | 0.083 |
| Xanthan Gum | 0.083 |
| Acrylate co-polymer | 0.05 |
| Sodium fluoride | 0.05 |

TABLE 3-continued

| Mouthwash 2: Ingredients | Concentration (% wt/wt) |
|---|---|
| Arginine (as L-Arginine) | 0.8 |
| Sweetener | 0.01 |
| Cetylpyridinium chloride | 0.05 |

TABLE 4

| Mouthwash 3: Ingredients | Theoretical Weight (%) |
|---|---|
| Water | 71.22 |
| Sorbitol (70% Soln.) | 10 |
| Glycerin | 7.5 |
| Propylene glycol | 7 |
| L-Arginine | 0.8 |
| Poloxamer 407 | 1 |
| Monobasic sodium phosphate | 1 |
| FD&C GREEN NO. 3 | 0.000375 |
| Cetylpyridinium chloride | 0.05 |
| Sodium benzoate | 0.5 |
| Flavor | 0.2 |
| Sodium phosphate dibasic | 0.15 |
| Sodium saccharin | 0.01 |
| Xanthan gum | 0.083 |
| Sodium CMC | 0.083 |
| Polyacrylate copolymer | 0.05 |
| Trimethyl glycine | 0.3 |
| Sodium fluoride | 0.05 |

Example 2

Exemplary compositions of the present invention can be prepared according to the following procedure:

Add approximately ⅓ of the water to a small vessel and slowly add in the acrylate co-polymer with strong mixing.
Add remaining water to the main mix tank.
Add the Poloxomer 407 and mix until fully dissolved.
Add the appropriate amount of sorbitol.
Add the sodium phosphate monobasic, sodium benzoate, anhydrous sodium phosphate dibasic, sodium saccharin, Betafin BP20, and L-Arginine and mix each in before adding the next.
Add the CPC and dye. Mix for 10 minutes to ensure the entire batch is completely solubilized.
Slurry the xanthan gum and CMC into the propylene glycol.
Add acrylate co-polymer and water mixture to the main mix tank.
Add xanthan gum and CMC slurry to the main mix tank and mix for 15 minutes.
Add flavor and mix for 5 minutes.

Example 3

The tri-polymer mouthwash formulations of Example 1 are evaluated for their rheological properties, in comparison with water, saliva, and three commercial mouthwashes. The three commercial mouthwashes are a simple fluoride-rinse type mouthwash (comparative formulation 1), a polymer based high fluoride mouthwash (comparative formulation 2), and a mouthwash having a conventional polymer system different from that described in this case (mouthwash 3). The rheological properties of the formulations are quantified using a stress controlled AR2000ex rheometer (TA Instruments) and a cuette type geometry. A flow curve is generated and fit to a power law model to quantify the flow rate index, n. A strain sweep is conducted to quantify the elastic modulus, G' and the loss modulus, G". The results are described in Table 5 (below).

TABLE 5

| Sample Name | Key Ingredients | G' (dyn/cm2) | G" (dyn/cm2) | G'/G" | k (cps) | n |
|---|---|---|---|---|---|---|
| Newtonian Fluid Example | Water | 0.02 | 0.23 | 0.09 | 1.1 | 1.0 |
| Viscoelastic Fluid Example | Natural saliva | 21.24 | 4.79 | 4.43 | 88.30 | 0.41 |
| Tri-Polymer Mouthwash 1 | Polymer Network + 90 ppm Fluoride + Arginine | 8.25 | 5.57 | 1.48 | 163.5 | 0.50 |
| Tri-Polymer Mouthwash 2 | Polymer Network + 225 ppm Fluoride + Arginine | 3.38 | 5.04 | 0.67 | 153.7 | 0.60 |
| Comparative Example 1 | 225 ppm fluoride | 0.06 | 0.69 | 0.09 | 5.35 | 1.00 |
| Comparative Example 2 | Polymer + 400 ppm Fluoride | 0.22 | 1.62 | 0.14 | 20.84 | 0.91 |
| Comparative Example 3 | Polymer + 225 ppm Fluoride + Arginine | 0.52 | 3.16 | 0.17 | 19.92 | 1.00 |

The data described in Table 5 (above) demonstrates that compositions of the present invention are viscoelastic (more like saliva), whereas the comparative examples are Newtonian (more like water).

Example 4

The tri-polymer mouthwashes are then compared with the commercial mouthwashes for their ability to protect against enamel loss. Enamel loss for the tri-polymer mouthwash prototypes are compared to water and the three commercial examples using an in vitro methodology based on the protocol published by S. M. Hooper, R. G. Newcombe, R. Faller, S. Eversole, M. Addy, N. X. West, *Journal of Dentistry*, 35 (2007), 476-481. Each formulation is tested with 4 to 6 replicates to obtain statistically meaningful results.

Bovine incisors are cleaned and sterilized with 70% alcohol. Each specimen is embedded in epoxy resin using a Teflon mold to form a 20 mm×10 mm×5 mm block. The enamel surface is ground using 600 and 1200 grit silicon carbide paper consecutively to achieve a shiny, flat surface. Each enamel surface is masked with tape, leaving only the center area (~0.5 mm wide) exposed. The masked enamel blocks are pre-etched with a 5% citric acid solution for 30 sec to create a pre-existing (incipient) lesion. All enamel samples are kept in artificial saliva at 37° C. for at least 12 hours prior to experimentation. The artificial saliva contained the following ingredients in 1000 mL of deionized water: 25 g mucin from porcine stomach, 466 mg $NH_4Cl$, 420 mg $CaCl_2.H_2O$, 86 mg $MgCl_2.6H_2O$, 2314 mg KCl, 708 mg $KH_2PO_4$, 444 mg KCNS, 1070 mg $NaHCO_3$, 750 mg $NaH_2PO_4$, 26 mg Sodium Citrate.$2H_2O$, 50 mg Albumin (BSA), 346 mg Urea, and 900 mg Glycine.

The erosion study is conducted through a cyclic de-mineralization and re-mineralization procedure. Each enamel substrate is treated with the assigned MW formulation or no-treatment H₂O control for 1 min in the morning, and then de-mineralized twice for 2 min using a 1% citric acid solution titrated to pH 3.8 with NaOH. The same procedure is repeated in the afternoon and this daily treatment regimen is repeated for 5 days. Except during de-mineralizations and MW treatments, the enamel substrates are always stored in artificial saliva at 37° C. Profilometry is used to quantify the enamel loss induced by acid exposure by measuring the step heights of the unmasked center relative to the masked regions. Enamel loss is computed using the step height difference before and after the cycling study.

The usage of the viscoelastic tri-polymer based prototypes results in a substantial and surprising decrease in enamel loss compared to that seen using the commercial comparator formulations, as seen in Table 6 (below).

TABLE 6

| Sample Name | Key Ingredients | Enamel Loss |
| --- | --- | --- |
| Water | Water | 0.4443 |
| Tri-Polymer Mouthwash 1 | Polymer Network + 90 ppm Fluoride + Arginine | 0.2258 |
| Tri-Polymer Mouthwash 3 | Polymer Network + 225 ppm Fluoride + Arginine | 0.2165 |
| Comparative Example 1 | 225 ppm fluoride | 0.3885 |
| Comparative Example 2 | Polymer + 400 ppm Fluoride | 0.4969 |
| Comparative Example 3 | Polymer + 225 ppm Fluoride + Arginine | 0.3877 |

The data described in Table 6 (above) demonstrates that compositions of the present invention unexpectedly provide a step height difference of less than 0.25 microns, when evaluated using the Hooper protocol described herein; whereas similarly formulated compositions which do not contain the inventive combinations described herein are unable to provide the same level of protection against enamel loss.

The invention claimed is:

1. An aqueous oral care composition comprising
    a) 0.5 to 2% by weight of a basic amino acid in free or orally acceptable salt form; and
    b) a polymer system comprising (i) 0.01 to 0.5% by weight of carboxy methyl cellulose, (ii) 0.01 to 0.5% by weight of xanthan gum, and (iii) 0.01 to 0.5% by weight of a polyacrylate polymer or co-polymer selected from a carbomer or a homo- or a copolymer of acrylic acid crosslinked with a polyalkenyl polyether;
    wherein the basic amino acid is selected from the group consisting of arginine hydrochloride, arginine phosphate, arginine bicarbonate, and combinations thereof;
    and wherein the composition comprises 50-90% by weight of water; and wherein the composition further comprises a fluoride source in an amount effective to provide about 225 ppm of fluoride;
    wherein the composition does not comprise an abrasive; and
    wherein the composition has a flow rate index of about 0.5 to about 0.6 and a G'/G" ratio of greater than 0.5.

2. The composition of claim 1, wherein the fluoride source is selected from sodium fluoride; sodium monofluorophosphate; and a combination thereof.

3. The composition of claim 1, wherein the fluoride source comprises sodium fluoride.

4. The composition of claim 1 wherein the basic amino acid is L-arginine in orally acceptable salt form.

5. The composition of claim 1, further comprising a buffering agent.

6. The composition of claim 1, further comprising a humectant.

7. The composition of claim 1, further comprising an antibacterial agent.

8. The composition of claim 1 wherein the polyacrylate polymer or co-polymer is a carbomer.

9. The composition of claim 1 wherein the polyacrylate polymer or co-polymer is selected from homo- and copolymers of acrylic acid crosslinked with a polyalkenyl polyether.

10. The aqueous oral care composition of claim 1, wherein the composition delivers an amount of fluoride effective to provide a step height difference of less than 0.25 microns, when evaluated using the Hooper protocol.

11. The composition of claim 10, wherein the fluoride source is present in the amount of about 0.05%, by weight, of the composition.

12. A method of reducing dental enamel erosion comprising administering a composition according to claim 1 to the oral cavity of subject in need thereof.

13. The method of claim 12, wherein the administering comprises rinsing for from 15 to 60 seconds.

14. The composition of claim 1 for use in a method of reducing dental enamel erosion.

15. The composition of claim 14 wherein the method comprises administering the composition to the oral cavity of a subject in need thereof.

16. The composition of claim 15 wherein the method further comprises rinsing for from 15 to 60 seconds.

* * * * *